United States Patent [19]
Jackson

[11] Patent Number: 5,488,122
[45] Date of Patent: Jan. 30, 1996

[54] ALKYL SUBSTITUTED METAL ALKYLALKOXYHYDROBORATE REDUCING AGENTS, AND PROCESSES FOR PRODUCTION AND USE OF THE SAME

[75] Inventor: Thomas C. Jackson, Seattle, Wash.

[73] Assignee: Complex Chemicals, Corp., Seattle, Wash.

[21] Appl. No.: 45,466

[22] Filed: Apr. 8, 1993

[51] Int. Cl.$^6$ ........................................................ C07F 5/02
[52] U.S. Cl. ............................................................. 556/8
[58] Field of Search ................................................. 556/8

[56] References Cited

U.S. PATENT DOCUMENTS 4,082,810  4/1978  Brown ............................. 260/606.5 B

OTHER PUBLICATIONS

Brown et al., "Selective Reductions. 26. Lithium Triethylborohydride as an Exceptionally Powerful and Selective Reducing Agent in Organic Synthesis. Exploration of the Reactions with Selected Organic Compounds Containing Representative Function Groups," *The Journal of Organic Chemistry*, vol. 45, No. 1, Jan. 4, 1980, pp. 1–2.

Brown et al., "Addition Compounds of Alkali Metal Hydrides. 27. A General Method of Preparation of the Potassium 9–Alkoxy-9–boratabicyclo[3.3.1]nonanes. A New Class of Stereoselective Reducing Agents," *The Journal of Organic Chemistry*, vol. 50, No. 5, Mar. 8, 1985, pp. 549–553.

Brown, "Interfacial Superbase Chemistry. The Catalyzed Reaction of Potassium Hydride with Trisiamylborane. A New Convenient Synthesis of Potassium Trisiamylborohydride," *The Journal of Organic Chemistry*, vol. 51, No. 2, 1986, pp. 238–240.

Brown et al, "An Unusual Reduction of Tertiary Amides with Carbon–Nitrogen Fission," *Inorganic Chemistry*, vol. 16, No. 9, 1977, pp. 635–637.

Brown et al., "Addition Compounds of Alkali Metal Hydrides. 13. Reactions of Alkali Metal Hydrides with Trialkylboranes Synthesis and Dissociation of Alkali Metal Trialkylborohydrides. Ethyl Ether–Organoborane as a Reversible 'Solvent' for Lithium Hydride," *Inorganic Chemistry*, vol. 16, No. 9, 1977, pp. 2229–2233.

Ashby et al., "Evidence for Single Electron Transfer in the Reduction of Organic Halides by Lithium Triethylborohydride," *The Journal of Organic Chemistry*, vol. 49, No. 23, 1984, pp. 4405–4509.

Yoon et al., "The Effect of Triethylborane in the Reduction of Epoxides with Lithium Borohydride," *Heterocycles*, vol. 22, No. 1, 1984, pp. 39–42.

Krishnamurthy et al., "Selective Reductions. 31. Lithium Triethylborohydride as an Exceptionally Powerful Nucleophile. A New and Remarkably Rapid Methodology for the Hydrogenolysis of Alkyl Halides under Mild Conditions," *The Journal of Organic Chemistry*, vol. 48, No. 18, 1983, pp. 3085–3091.

Brown et al., "Selective Reductions. 32. Structural Effects on the Reduction of Epoxides by Lithium Triethylborohydride. A Kinetic Study," *The Journal of Organic Chemistry*, vol. 48, No. 18, 1983, pp. 3091–3096.

Brown et al., "Selective Reductions. 35. Reaction of Representative Organic Functional Groups with Lithium Borohydride in the Presence of β–Methoxy-9–borabicyclo[3.3.1] nonane. A Simple, Convenient Procedure for the Catalyzed Selective Reduction of Esters," *The Journal of Organic Chemistry*, vol. 49, No. 21, 1984, pp. 3891–3898.

Brown et al., "New Powerful Catalysts for the Reduction of Esters by Lithium Borohydride," *The Journal of Organic Chemistry*, vol. 47, No. 8, 1982, pp. 1604–1606.

Brown et al., "Selective Reductions. 36. Reaction of Lithium 9–Boratabicyclo[3.3.1]nonane with Selected Organic Compounds Containing Representative Functional Groups," Reprinted from *The Journal of Organic Chemistry*, vol. 49, No. 17, 1984, pp. 3091–3097.

Narasimhan, "Methanol–catalysed Addition of Lithium Hydride to 9–Borabicyclo–[3.3.1]nonane," *Indian Journal of Chemistry*, vol. 25B, Aug. 1986, pp. 847–848.

Brown et al., "Hydroboration. 45. New, Convenient Preparations of Representative Borane Reagents Utilizing Borane–Methyl Sulfide," *The Journal of Organic Chemistry*, vol. 42, No. 8, 1977, pp. 1392–1398.

Brown et al., "Addition Compounds of Alkali–Metal Hydrides. 24. A General Method for Preparation of Potassium Trialkoxyborohydrides. A New Class of Reducing Agents," *Inorganic Chemistry*, vol. 23, No. 19, 1984, pp. 2929–2931.

Brown et al., "A New, Highly Stereoselective Reducing Agent, Potassium 9–(2,3–Dimethyl–2–butoxy)9–boratabicyclo[3.3.1]nonane," *The Journal of Organic Chemistry*, ©1984 American Chemical Society, pp. 2703–2074.

Brown et al., "Addition Compounds of Alkali Metal Hydrides. 28. Preparation of Potassium Dialkoxymonoalkylborohydrides from Cycle Boronic Esters. A New Class of Reducing Agents," *The Journal of Organic Chemistry*, vol. 51, No. 3, 1986, pp. 337–342.

Brown et al., "Potassium, 9–O–(1,2:5,6–Di–O–isopropylidene–α–D–glucofuranosyl)–9– boratabicyclo[3.3.1]nonane. A New, Effective Chiral Borohydride Reagent," *The Journal of Organic Chemistry*, vol. 51, No. 10, pp. 1934–1936, 1986.

Brown et al., "Addition Compounds of Alkali Metal Hydrides. 29. Preparation and Properties of Chiral Dialkylmonoalkoxyborohydrides. A New Class of Asymmetric (List continued on next page.)

*Primary Examiner*—Porfirio Nazario-Gonzales
*Attorney, Agent, or Firm*—Christensen, O'Connor, Johnson & Kindness

[57] ABSTRACT

Alkyl substituted metal hydroborate reducing agents are produced by reacting a borane or mono- or di-alkylborane with greater than 10%, based on the molar content of the borane, of a metal alkoxide, metal alkylthiolate, metal alkylamide, halogenated metal alkoxide, halogenated metal alkylthiolate or halogenated alkylamide.

8 Claims, No Drawings

OTHER PUBLICATIONS

Reducing Agents," *The Journal of Organic Chemistry*, vol. 51, No. 17, 1987, pp. 3273–3282.

Brown et al., "Additional Compounds of Alkali Metal Hydrides. 31. Preparation and Properties of Chiral Dialkoxymonoalkylborohydrides. A New Class of Asymmetric Reducing Agents," *The Journal of Organic Chemistry*, vol. 52, No. 18, 1987, pp. 4020–4024.

Krishnamurthy et al., "Trialkylborohydrides as New Versatile Reducing Agents in Organic Synthesis," Purdue University, pp. 55–60, 1974.

Brown et al., "Addition Compounds of Alkali–Metal Hydrides. 23. Preparation of Potassium Triisopropoxyborohydride in Improved Purity",: *Organometalics*, vol. 2, No. 5, 1983, pp. 634–637.

Cha et al., "Enantioselective Reduction of Racemic Epoxides with the Chiral 9–Alkoxy–9–Borabicyclo[3.3.1] nonane–Potassium Hydride and Chiral Potassium 9–Alkoxy–9–Boratabicyclo[3.3.1]nonane Systems," *Heterocycles*, vol. 27, No. 7, 1988, pp. 1713–1717.

ALKYL SUBSTITUTED METAL ALKYLALKOXYHYDROBORATE REDUCING AGENTS, AND PROCESSES FOR PRODUCTION AND USE OF THE SAME

FIELD OF THE INVENTION

The present invention relates to reducing agents, and more particularly to alkyl substituted metal hydroborate reducing agents.

BACKGROUND OF THE INVENTION

Alkali metal borohydrides have been commercially recognized as powerful nucleophilic reducing agents. The first such borohydride to be recognized was lithium triethylborohydride, which has been found to reduce most organic functional groups in a matter of minutes under very mild conditions at room temperature. Other lithium mono- and di-alkylborohydrides have since been prepared and have been determined to have suitable reducing characteristics for various organic functional groups. One commercially available reducing agent in this category is lithium 9-boratabicyclo(3.3.1)nonane (hereinafter "Li9-BBNH"). This reagent is prepared by reacting lithium hydride with 9-BBN in tetrahydrofuran as a solvent. The reaction is extremely slow, taking 48 hours at 25° C. In industry, this reaction is typically carried out at 65° C. for a period of 24 hours.

The prolonged high temperature reflux required to produce such lithium mono- and di-alkylborohydrides greatly limits the structural range of products resulting. This is because mono- and di-alkylboranes readily disproportionate within hours at reflux temperatures.

In addition to requiring long preparation times and resulting in a small variety of products, such known lithium mono- and di-alkylborohydrides do not make efficient use of the metal hydride moiety included therein when used to reduce organic functional groups. For example, the reducing agent lithium triethylborohydride ($LiEt_3BH$) reacts with a reducible functional group to produce the byproduct triethylborane. This byproduct then reacts with the remaining lithium triethylborohydride to form $LiEt_3BH:BEt_3$. This latter compound is relatively inactive. In effect, the reducing agent serves as its own inactivator and therefore requires at least a 100% excess for reduction. The conventional reducing agent Li9-BBNH behaves similarly, reacting with many organic compounds to liberate less reactive 9-BBN.

Finally, an additional drawback of such conventional lithium mono- and di-alkylborohydride reducing agents is that they must be inactivated prior to recovery of the desired reduction product, which usually entails an oxidative workup that many organic compounds can not tolerate.

SUMMARY OF THE INVENTION

The present invention is directed to alkyl substituted metal hydroborate reducing agents produced by reacting alkylboranes with metal salts. In a preferred embodiment of the invention, mono- or di-alkylboranes are reacted with metal alkoxides, metal alkylthiolates, metal alkylamides, halogenated metal alkoxides, halogenated metal alkylthiolates, or halogenated metal alkylamides.

The present invention is also directed to processes for producing alkyl substituted metal hydroborate reducing agents of the formula $X_iM[R_lR_mB(AR_jR_k)_{p+1-r}H_r]_{n-i}$ by reacting an alkylborane having the formula $R_lR_mBH_p$ with a metal salt of the formula $X_iM(AR_jR_k)_{n-i}$, wherein:

X is a halogen;

M is a metal;

A is selected from the group consisting of oxygen, sulfur and nitrogen;

$R_j$, $R_k$, $R_l$, and $R_m$ are each hydrocarbons selected from the group consisting of hydrogen, C1–C24 alkyl, aryl, arylalkyl, monocyclic, polycyclic, and heterocyclic radicals, wherein $R_j$ and $R_k$ may share a covalent bond, and $R_l$ and $R_m$ may share a covalent bond;

i equals an integer between 0 and 2;;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3.

The alkyl substituted metal hydroborate reducing agents of the present invention tend to disproportionate, yielding a heterogeneous reducing agent system that behaves as a homogeneous reducing agent. The reducing agents of the present invention are easily prepared, and can be derived by allowing the reaction of the present invention to proceed for from 1 to 6 hours at room temperature.

Because the long time duration, high temperature reflux required for production of prior known alkali metal borohydrides is not required to produce the reducing agents of the present invention, the reducing agents of the present invention are much less expensive to produce. The reducing agents of the present invention are quite powerful, however, reducing a broad variety of organic functional groups in time intervals ranging from less than 5 minutes to less than 24 hours. The byproducts of reduction are easily removed from the reduced product solution. The reducing agents of the present invention are also "efficient" in use of the available hydride, avoiding the above-noted problem of self-inactivation common with previously known alkali metal borohydrides.

DETAILED DESCRIPTION OF THE PREFERRED EMBODIMENT

The alkyl substituted metal hydroborate reducing agents of the present invention are the reaction products of: a borane or mono- or di-alkylborane with a metal salt. The metal salt may be a metal alkoxide, a metal alkylthiolate or a metal alkylamide. Additionally, halogenated versions of these metal salts may be used. The reducing agents of the present invention and reaction to produce the same is represented by the following equation:

$$R_lR_mBH_p + X_iM(AR_jR_k)_{n-i} \rightarrow X_iM[R_lR_mB(AR_jR_k)_{p+1-r}H_r]_{n-i} \quad (1)$$

wherein:

X is a halogen;

M is a metal;

A is selected from the group consisting of oxygen, sulfur and nitrogen;

$R_j$, $R_k$, $R_l$ and $R_m$ are each hydrocarbons selected from the group consisting of hydrogen, C1–C24 alkyl, aryl, arylalkyl, monocyclic, polycyclic, and heterocyclic radicals, wherein $R_j$ and $R_k$ may share a covalent bond, and $R_l$ and $R_m$ may share a covalent bond;

i equals an integer between 0 and 2;;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3.

Metal Salts

Suitable metal salts for Equation 1 are metal alkoxides (i.e., when A in Equation 1 is oxygen), metal alkylthiolates (when A is sulfur) or metal alkylamides (when A is nitrogen), or mixtures of these. Additionally, halogenated metal alkoxides, alkylthiolates and alkylamides are suitable for use. Preferred halogenated metal salts contain fluorine, chlorine, bromine, iodine or astatine.

The metal salt may contain one or two hydrocarbon moieties, which as used herein includes hydrogen, C1–C24 alkyl, aryl, arylalkyl, monocyclic, bicyclic, polycyclic, and heterocyclic radicals. When two hydrocarbon moieties are included, the two moieties may be either identical or different, and may share a covalent bond. Preferred alkyl radicals are methyl, ethyl, n-propyl, isopropyl, n-butyl, isobutyl, sec-butyl, t-butyl, n-pentyl, isopentyl, hexyl, heptyl, octyl, nonyl, and decyl radicals. Alkyl radicals may be either branched or straight chained.

Suitable aryl moieties include phenyl, benzyl, p-tolyl and ethers such as $C_6H_4OCH_3$. Examples of other suitable cyclic radicals are radicals of pentane, cyclohexane, napthalene, anthracene, phenanthrene, cumene, styrene, o-xylene, isopinocampheyl, and furanes.

Suitable metals for the metal salts include alkali metals, such as lithium, sodium, and potassium, rare metals such as beryllium, magnesium and calcium, as well as zinc and aluminum.

When the metal salt is a metal alkoxide or halogenated metal alkoxide, the reducing agent obtained in accordance with the present invention is a metal alkyl alkoxy hydroborate. Non-limiting examples of metal alkoxides suitable for practice of the present invention are: lithium methoxide, sodium methoxide, dichloroaluminum isoprop-oxide, sodium isopropoxide, sodium cyclohexoxide, bromomagnesium thexoxide, zinc ethoxide, and magnesium bis(n-hexoxide).

Rather than using an alkoxy metal salt, metal alkylthiolates (i.e., A is sulfur in Equation 1) may be used to produce alkyl substituted metal alkylthiolate reducing agents. In general, the sulfur versions of the alkoxy compounds previously listed are suitable for use with the present invention. Examples of particular alkylthiolates found to be suitable include sodium methylthiolate, sodium ethylthiolate, lithium methylthiolate, chloromagnesium phenylthiolate, dilithium ethane dithiolate, and dichloroaluminum propylthiolate.

Metal alkylamides and halogenated metal alkylamides are also suitable as metal salts for use in the present invention (i.e., when A is nitrogen in Equation 1). Suitable alkylamides include lithium amide, lithium di-isopropylamide, sodium ethaneamide and magnesium(pyrrolidineamide)$_2$.

Alkylboranes

As used herein, the term alkylboranes refers to boranes, monoalkylboranes, and di-alkylboranes. Mono- and di-alkylboranes are suitable for use in reacting with metal alkoxides, metal alkylthiolates and metal alkylamides to produce the reducing agents of the present invention. Additionally borane may be utilized for reaction with metal alkylthiolates and metal alkylamides.

Suitable hydrocarbon moieties for mono- and di-alkylboranes for use in the present invention include those hydrocarbon radicals listed above as suitable for metal salts of the present invention. Thus, hydrogen, C1–C24 alkyl, aryl, arylalkyl, monocyclic, bicyclic, and heterocyclic alkyls may be used. Most preferably, when the metal salt is a metal alkoxide, the hydrocarbon moiety is a C1–C24 alkyl, aryl, arylalkyl, monocyclic, polycyclic, mono-heterocyclic, or bi-heterocyclic, wherein one of the rings bonded to boron is non-heterocyclic (i.e., a heterocyclic ring joined to a non-heterocyclic hydrocarbon ring). When the alkylborane is a di-alkylborane, the two alkyl groups may be either identical or different, and may share a covalent bond.

Non-limiting examples of suitable mono- or di-alkylboranes for use in the practice of the present invention include 9-boratabicyclo[3.3.1]nonane, disiamylborane, methylborane, diisopinocampheylborane, phenylborane, monoisopinocampheylborane, dicyclohexylborane, and, for reacting with metal alkylthiolates and metal alkylamides, borane.

Alkyl Substituted Metal Hydroborate Reducing Agents

The alkyl substituted metal organoboranes of the present invention are those produced by reaction of Equation 1, and include alkali metal hydroborates and other metal alkylalkoxyhydroborates, alkyl substituted metal alkylthiolates and alkyl substituted metal alkylamides, as well as alkyl substituted halogenated metal alkoxides, alkylthiolates and alkylamides.

When the metal salt utilizes an alkylthiolate, the alkyl substituted metal hydroborate reducing agent produced is the one-to-one addition product of the metal alkylthiolate and the alkylborane. No significant amount of disproportionation of the reducing agent product is found. However, when the metal salt is either a metal alkoxide or metal alkylamide, the resulting alkyl substituted metal alkoxide or alkylamide readily disproportionates. The reducing agent system represented by these disproportionated products behaves as a homogeneous reducing agent species, however, as will be shown by the examples following below.

Non-limiting examples of alkyl substituted metal hydroborate reducing agents of the present invention include: lithium 9-boratabicyclo[3.3.1]-nonane, lithium 9,9-dimethoxy-9-boratabicyclo[3.3.1]-nonane, dichloroaluminum disiamylborohydride, dichloroaluminum disiamyldiisopropoxyborate, lithium methylborohydride, lithium methyltrimethoxyborate, sodium thexylmonoisopropoxyborohydride, sodium thexyldiisopropoxyborohydride, sodium thexyltriisopropoxyborohydride, sodium thexylborohydride, sodium diisopinocampheyldicycohexoxyborate, sodium diisopinocampheylborohydride, bromomagnesium phenylborohydride, bromomagnesium phenylmonothexoxyborohydride, bromomagnesium phenyldithexoxyborohydride, bromomagnesium phenyltrithexoxyborate, zinc monoisopinocampheylborohydride, zinc monoisopinocampheyltriethoxyborate, magnesium dicyclohexylborohydride, magnesium dicyclohexyldinhexoxyborate, sodium 9-methyl thiolate-9-boratabicyclo [3.3.1] nonane, $NaBH_3SCH_3$, and lithium 9,9-diisopropylamide 9-boratabicyclo [3.3.1] nonane.

Process for Producing Alkyl Substituted Metal Hydroborates

To produce the alkyl substituted metal hydroborate reducing agents of the present invention, the alkylborane is preferably added to a solution or slurry of the metal salt in a hydrocarbon solvent. Non-limiting examples of suitable hydrocarbon solvents are: tetrahydrafuran, ethyl ether, methylsulfide, cyclohexane, pentane, and mixtures thereof. Preferred solvents are tetrahydrafuran and ethyl ether, or hydrocarbon mixtures including tetrahydrafuran or ethyl ether. While use of a solvent is preferred, in some instances the reactants will act as their own solvents.

Preferably, the metal salt is present at a concentration of greater than 10% of the molar concentration of the alkylborane. Most preferably the metal salt and the alkylborane are combined in substantially stoichiometric ratios.

The alkyl substituted metal hydroborate reducing agents of the present invention are produced by allowing the metal salt and alkylborane to react at ambient temperatures. The exact reaction time required will depend on the species being reacted, as can be readily determined by one of ordinary skill in the art in view of the disclosure contained herein. For most of those species disclosed herein, it has been found that the reaction is substantially complete within one hour at 25° C. For all of the reaction species disclosed herein, it has been found that the reaction is substantially complete within a time period of from 1 to 6 hours at 25° C. The reaction temperature can be elevated to temperatures greater than 25° C. to increase the reaction speed, however this is not required.

The alkyl substituted metal hydroborate reducing agent produced by the above reaction, or disproportionated products thereof, can be either recovered from the solvent as a solid or left in solution for use in reducing an organic functionality susceptible to reduction.

The alkyl substituted metal hydroborates of the present invention have been found to be powerful reducing agents for a wide variety of organic functional groups that are susceptible to reduction. For example, the reducing agents of the present invention have been found to reduce aldehyde, ketone, acid chloride and lactone functionalities within five minutes at 25° C. Ester functionalities have been found to be reduced within one-half hour at 25° C. Epoxides are reduced within six hours at 25° C. Alkylbromides and iodides are also reduced rapidly (0.5 to 2 hours) by the reducing agents of the present invention, while alkylchlorides are also reduced within 24 hours at 25° C. Tertiary amide and nitrile functionalities, however, are inert to the reducing agents of the present invention over a period of 48 hours. The boron derivative produced by reducing organic functionalities with the reducing agents of the present invention can be readily removed by extraction, chelation, or filtration, as will be readily determined by those with skill in the art based on the disclosure contained herein.

Additional Reducing Agents From Boronic and Borinic Acids and Esters

The boron derivative produced by reduction with the alkyl substituted metal hydroborate reducing agents of the first embodiment of the present invention described above are boronic acids and esters, or borinic acids and esters, (when the metal salt utilized is a metal alkoxide) or alkylthiol boranes (when the metal salt is a metal alkylthiolate), or alkylamidoboranes (when the metal salt is a metal alkylamide). As noted above, these borane byproducts are readily removed from the reduction reaction mixture by filtration, chelation, or extraction.

In a further aspect of the present invention, it has been found that these borane derivatives may be further reacted with metal hydrides or metal halides to produce further reducing agents, hereinafter referred to as the second embodiment of reducing agents. These reducing agents can be represented by the following formula:

$$X_iMH_{j-i}+(R'A)_tB\ R_nR_pH_r \rightarrow X_iM[R_nR_pB(R'A)_{4-n-p-m}H_m]_{j-i} \quad (2)$$

X is a halogen (F, Cl, Br, I, At);
i equals an integer between 0 and 4;

M is a metal selected from the group consisting of Li, Na, K, Be, Mg, Ca, Zn and Al;
j equals an integer between 0 and 4;
A is selected from the group consisting of oxygen, sulfur and nitrogen;
t equals 1 or 2;
R', Rn, Rp, are each hydrocarbons selected from the group consisting of C1–C24;
alkyl, aryl, arylalkyl, monocyclic, polycylic and heterocyclic radicals;
n and p each equal 0 or 1;
r equals 3 minus the sum of t, n and p; and
m equals an integer between 0 and 3.

Preferred boronic acids, boronic esters, borinic acids and borinic esters are those that will react with the metal hydride or metal halide to form a tetravalent boron reducing agent. Again, as for the first preferred embodiment of the present invention, the boron reducing agent tends to disproportionate, yielding products including between zero and three alkoxy, alkylthiol and alkylamido moeties. These disproportionated species act as a single, homogeneous reducing system.

The metal halide or metal hydride and the borane derivative are preferably reacted in the presence of a suitable hydrocarbon solvent, including those previously disclosed for the first preferred embodiment of the present invention. Preferred solvents include tetrahydrafuran or ethyl ether. The reaction is essentially complete within from one to six hours at room temperature.

EXAMPLES

The following experiments to produce reducing agents in accordance with the first preferred embodiment of the present invention were carried out under an inert atmosphere of nitrogen using oven or flame dried equipment. Each experiment was carried out at 25° C., unless otherwise noted.

Example 1

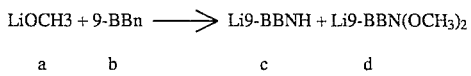

a      b          c        d

The above reaction was carried out in a 1 liter round bottom flask with reflux condenser and septum inlet. Methanol, 12.62 mL (312 mmol) was diluted with 351.7 mL of tetrahydrofuran, THF. To this stirred solution, 312 mmoles of n-butyl lithium (124.8 mL of a 2.5M solution in hexanes) was added at 0° C., yielding a total of 500 mL of a well suspended slurry of lithium methoxide, a, LiOMe. The reflux condenser was replaced with a simple distillation setup and approximately 100 mL of solvent was removed at atmospheric pressure and 65° C. This process removes dissolved butane and allows the final solution of the borohydride to be standardized with a hydride meter. This slurry was added via double ended needle to 38.13 g (312 mmol) of solid 9-borabicyclo[3.3.1]nonane, b, 9-BBN in a 1 liter flask. The contents of the flask quickly pass into solution at 25° C. within one hour, with a small amount of precipitate formed. The final solution has a milky appearance due to its concentration. This solution was transferred into a 500 mL volumetric flask, and THF was added to bring the total volume to 500 mL. After cooling overnight the solution was standardized using a hydride meter and found to be 0.56M in hydride, corresponding to a yield of 89.7%. This solution was analyzed using $^{11}$B NMR (Bruker 250 MHz) and found to be a mixture of lithium 9-boratabicyclo[3.3.1]-nonane, c, and lithium 9,9-dimethoxy-9-boratabicyclo[3.3.1]nonane, d.

Example 2

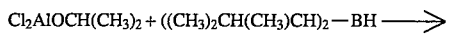
    a            b

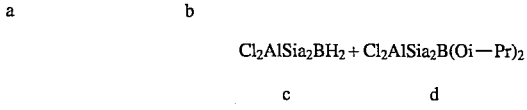

Isopropanol (0.766 mL, 0.601 g, 10 mmol) was diluted to 10 mL with 9.23 mL of n-hexanes. To this stirred solution, 10 mL of a 1M solution of ethyl aluminum dichloride was added slowly at 0° C. Gas was evolved with each drop. This reaction resulted in a slurry of 10 mmol of dichloroaluminum isopropoxide, a, as an approximate 0.5M solution in hexanes. To this slurry was added a solution of disiamylborane, b, in ethyl ether, 10 mL of a 1M solution. After one hour at 25° C. the mixture was analyzed and found to contain dichloroaluminum disiamylborohydride, c, and dichloroaluminum disiamyldi-isopropoxyborate, d, and to be devoid of starting material disiamylborane, b.

Example 3

  a       b            c         d

Solid lithium methoxide, a, (0.418 g, 11 mmol) was diluted with 10 mL of ethyl ether. To this stirred slurry was added 20 mL of a 0.5M solution of freshly prepared methyl borane, b. The mixture was stirred for two hours at 25° C. Analysis of the mixture via $^{11}$B NMR revealed both lithium methylborohydride, c, and lithium methyltrimethoxyborate, d, and an absence of the starting material methyl borane, b.

Example 4

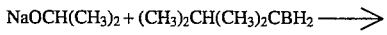
    a            b

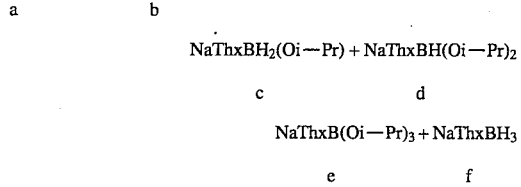

Solid sodium isopropoxide, a, (0.902 g, 11 mmol) was mixed with 10 mL THF. Thexylborane, b, (ThxBH$_2$) (0.98 g, 10 mmol) in 9 mL of THF/Methyl Sulfide was added to the slurry and stirred for one hour. Analysis indicated the formation of various products: sodium thexylmonoisopropoxyborohydride, c, sodium thexyldiisopropoxy-borohydride, d, sodium thexyltriisopropoxyborate, e, and sodium thexylborohydride, f, and the complete disappearance of starting material thexylborane, b.

Example 5

 a       b          c           d

Ten milliliters of a previously prepared slurry of THF containing 1.34 g of sodium cyclohexoxide, a, (10 mmols) was added to a flask containing solid diisopinocampheylborane, b, (2.86 g, 10 mmol), free of solvent. The mixture was stirred and an additional 10 mL of THF was added. The solid Ipc$_2$BH quickly broke up and dissolved, however, another precipitate formed concurrently with this and was believed to be the compound sodium diisopinocampheyldicyclohexoxyborate, d. Analysis of the mixture revealed an absence of the starting borane, b, and the formation of sodium diisopinocampheyl-borohydride, c.

Example 6

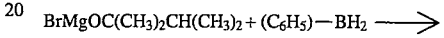
    a          b

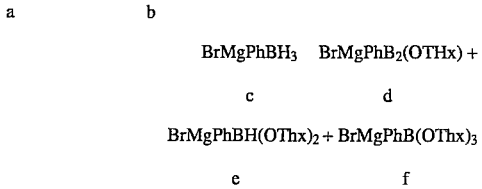

Tertiary hexanol (2,3-dimethyl-2-butanol, HOThx), 1.02 g, 10 mmol, was diluted to a 1M solution with THF (9.2 mL). To this stirred solution, 3.33 mL of a 3.0M solution of methyl magnesium bromide in diethyl ether was added dropwise while the solution was maintained at 0° C. This results in a clear solution of bromomagnesium thexoxide, a. A 1.0M solution of phenylborane, b, in hexanes(9.5 mL, 9.5 mmol) was added rapidly to this solution, and a small amount of precipitate formed. $^{11}$B NMR indicated the presence of the following compounds: bromomagnesium phenylborohydride, c, bromomagnesium phenyl monothexoxyborohydride, d, bromomagnesium phenyldithexoxyborohydride, e, and bromomagnesium phenyltrithexoxyborate, f, and an absence of the starting material phenylborane, b.

Example 7

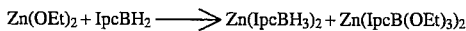
  a        b          c          d

Freshly prepared monoisopinocampheylborane, b, (1.5 g, 10 mmol) as a 1.0M solution in ethyl ether was added via double ended needle to solid zinc ethoxide, a, 1.7 g, 11 mol. To this slurry, 10 mL of THF was added, and the mixture stirred for 6 hours. Analysis of the solution revealed the presence of zinc monoisopinocampheylborohydride, c, and zinc monoisopinocampheyltriethoxyborate, d, and the absence of starting material monoisopinocampheyl borane, b.

Example 8

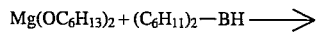
    a          b

-continued

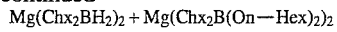

Ten milliliters of THF was added to 10 mmol, 2.26 g of solvent free magnesium bis (n-hexoxide), a, previously prepared from magnesium hydride and n-hexanol in ethyl ether. The slurry was stirred for one hour and transferred via double ended needle to a flask containing 10 mmol, 1.78 g of solidified dicyclohexylborane, b, in ethyl ether, methyl sulfide, and excess cyclohexene. The solid quickly broke up and dissolved. Analysis of the solution revealed the presence of magnesium dicyclohexylborohydride, c, and magnesium dicyclohexyldin-hexoxyborate, d, and the absence of starting material dicyclohexylborane, b.

Example 9

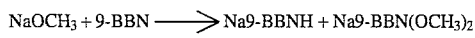

The above reaction was carried out using the procedure of Example 1, except that sodium methoxide was used in place of lithium methoxide. A clear solution resulted within an hour at 25° C. The solution was analyzed using $^{11}$B NMR, and was found to include equal amounts of sodium 9-boratabicyclo-[3.3.1]nonane, c, and sodium 9,9-dimethoxy-9-boratabicyclo-[3.3.1]nonane, d.

Example 10

The above reaction was carried out using the procedure of Example 1, except that sodium methyl thiolate, a, was used in place of lithium methoxide. A clear solution resulted within an hour at 25° C. The solution was analyzed using $^{11}$B NMR, and was found to include sodium 9-methyl thiolate-9-boratabicyclo[3.3.1]nonane, c, in the non-disproportionated form.

Example 11

The above reaction was carried out using the procedure of Example 10, except that borane, b, was used in place of 9-BBN. A clear solution resulted within an hour at 25° C. The solution was analyzed using $^{11}$B NMR, and was found to include NaBH$_3$SCH$_3$, c, in the non-disproportionated form.

Example 12

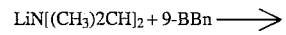

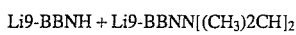

The above reaction was carried out using the procedure of Example 1, except that lithium diisopropylamide, a, was used in place of lithium methoxide. A clear solution resulted within an hour at 25° C. The solution was analyzed using $^{11}$B NMR, and was found to include a mixture of lithium 9-boratabicyclo[3.3.1]nonane, c, and lithium 9,9-diisopropylamide 9-boratabicyclo[3.3.1]nonane, d.

While the preferred embodiments of the invention have been described and examples thereof provided, it will be appreciated that various changes can be made therein by those of ordinary skill in the art based on the disclosure herein, without departing from the spirit and scope of the present invention. Thus it is intended that the scope of letters patent granted hereon be limited only by the definitions of the appended claims.

The embodiments of the invention in which an exclusive property or privilege is claimed are defined as follows:

1. A process for producing an alkyl substituted metal hydroborate reducing agent of the formula $X_iM[R_lR_mB(AR-jR_k)_{p+1-r}H_r]_{n-i}$ comprising: reacting an alkylborane having the formula $R_lR_mBH_p$ with greater than 10%, based on the molar content of the alkylborane, of a metal salt of the formula $X_iM(AR_jR_k)_{n-i}$, wherein:

X is a halogen, wherein the halogen is selected from the group consisting of fluorine, chlorine, bromine, iodine, and astatine;

M is a metal;

A is selected from the group consisting of oxygen, sulfur and nitrogen;

$R_j$, $R_k$, $R_l$, and $R_m$ are each hydrocarbons selected from the group consisting of hydrogen, C1–C24 alkyl, aryl, arylalkyl, monocyclic, polycyclic, and heterocyclic radicals, wherein $R_j$ and $R_k$ may share a covalent bond, and $R_l$ and $R_m$ may share a covalent bond;

i equals an integer between 0 and 2;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3.

2. A process for producing an alkyl substituted metal hydroborate reducing agent of the formula $X_iM[R_lR_mB(AR-jR_k)_{p+1-r}H_r]_{n-i}$ comprising: reacting an alkylborane having the formula $R_lR_mBH_p$ with greater than 10%, based on the molar content of the alkylborane, of a metal salt of the formula $X_iM(AR_jR_k)_{n-i}$, wherein:

X is a halogen;

M is a metal;

A is oxygen;

$R_j$, $R_k$, $R_l$, and $R_m$ are each hydrocarbons selected from the group consisting of hydrogen, C1–C24 alkyl, aryl, arylalkyl, monocyclic, polycyclic, and heterocyclic radicals, wherein $R_j$ and $R_k$ may share a covalent bond, $R_l$ and $R_m$ may share a covalent bond;

i equals an integer between 0 and 2;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3, wherein the process yields an alkyl substituted metal hydroborate reducing agent selected from the group consisting of lithium 9-boratabicyclo[3.3.1]-nonane, lithium 9,9-dimethoxy-9-boratabicyclo-[3.3.1]-nonane, dichloroaluminum disiamylborohydride, dichloroaluminum disiamyldiisopropoxyborate, lithium methylborohydride, lithium methyltrimethoxyborate, sodium thexylmonoisopropoxyborohydride, sodium thexyldiisopropoxyborohydride, sodium thexyltriisopropoxyborohydride, sodium thexylborohydride, sodium diisopinocampheyldicycohexoxyborate, sodium diisopinocampheylborohydride, bromomagnesium phenylborohydride, bromomagnesium phenylmonothexoxy-borohydride, bromomagnesium phenyldithexoxyborohydride, bromomagnesium phenyltrithexoxyborate, zinc monoisopinocampheylborohydride, zinc monoisopinocampheyltriethoxyborate, magnesium dicyclohexylborohydride, and magnesium dicyclohexyldin-hexoxyborate.

3. A process for producing an alkyl substituted metal hydroborate reducing agent of the formula $X_iM[R_lR_mB(AR_jR_k)_{p+1-r}H_r]_{n-i}$ comprising: reacting an alkylborane having the formula $R_lR_mBH_p$ with a metal salt of the formula $X_iM(AR_jR_k)_{n-i}$, wherein:

X is a halogen, wherein the halogen is selected from the group consisting of fluorine, chlorine, bromine, iodine, and astatine;

M is a metal;

A is selected from the group consisting of oxygen, sulfur and nitrogen;

$R_j$, $R_k$, are each hydrocarbon radicals, which may share a covalent bond, selected from the group consisting of hydrogen, C1–C24 alkyl, aryl, arylalkyl, monocyclic, polycyclic, and heterocyclic;

$R_l$, and $R_m$ are each hydrocarbon radicals, which may share a covalent bond, selected from the group consisting of hydrogen, C1–C24 alkyl, aryl, arylalkyl, monocyclic, bicyclic and monoheterocyclic;

i equals an integer between 0 and 2;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3.

4. A process for producing an alkyl substituted metal hydroborate reducing agent of the formula $X_iM[R_lR_mB(AR_jR_k)_{p+1-r}H_r]_{n-i}$ comprising: reacting an alkylborane having the formula $R_lR_mBH_p$ with a metal salt of the formula $X_iM(AR_jR_k)_{n-i}$, wherein:

X is a halogen;

M is a metal;

A is oxygen;

$R_j$, $R_k$, are each hydrocarbon radicals, which may share a covalent bond, selected from the group consisting of hydrogen, C1–C24 alkyl, aryl, arylalkyl, monocyclic, polycyclic, and heterocyclic;

$R_l$, and $R_m$ are each hydrocarbon radicals, which may share a covalent bond, selected from the group consisting of hydrogen, C1–C24 alkyl, aryl, arylalkyl, monocyclic, bicyclic and monoheterocyclic;

i equals an integer between 0 and 2;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3, wherein the process yields an alkyl substituted metal hydroborate reducing agent selected from the group consisting of lithium 9-boratabicyclo[3.3.1]-nonane, lithium 9,9-dimethoxy-9-boratabicyclo-[3.3.1]-nonane, dichloroaluminum disiamylborohydride, dichloroaluminum disiamyldiisopropoxyborate, lithium methylborohydride, lithium methyltrimethoxyborate, sodium thexylmonoiso-propoxyborohydride, sodium thexyldiisopropoxyborohydride, sodium thexyltriisopropoxyborohydride, sodium thexylborohydride, sodium diisopinocampheyldicycohexoxyborate, sodium diisopinocampheylborohydride, bromomagnesium phenyl-borohydride, bromomagnesium phenylmonothexoxyborohydride, bromomagnesium phenyldithexoxyborohydride, bromomagnesium phenyltrithexoxyborate, zinc monoisopinocampheylborohydride, zinc monoisopinocampheyltriethoxyborate, magnesium dicyclohexylborohydride, and magnesium dicyclohexyldin-hexoxyborate.

5. An alkyl substituted metal hydroborate reducing agent of formula: $X_iM[R_lR_mB(AR_jR_k)_{p+1-r}H_r]_{n-i}$ wherein:

X is a halogen, wherein the halogen is selected from the group consisting of fluorine, chlorine, bromine, iodine, and astatine;

M is a metal;

A is selected from the group consisting of oxygen, sulfur and nitrogen;

$R_j$, $R_k$, are each hydrocarbon radicals, which may share a covalent bond, selected from the group consisting of hydrogen, C1–C24 alkyl, aryl, arylalkyl, monocyclic, polycyclic, and heterocyclic;

$R_l$, and $R_m$ are each hydrocarbon radicals, which may share a covalent bond, selected from the group consisting of hydrogen, C1–C24 alkyl, aryl, arylalkyl, monocyclic, bicyclic and monoheterocyclic;

i equals an integer between 0 and 2;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3.

6. An alkyl substituted metal hydroborate reducing agent of formula: $X_iM[R_lR_mB(AR_jR_k)_{p+1-r}H_r]_{n-i}$ wherein:

X is a halogen;

M is a metal;

A is oxygen;

$R_j$, $R_k$, are each hydrocarbon radicals, which may share a covalent bond, selected from the group consisting of hydrogen, C1–C24 alkyl, aryl, arylalkyl, monocyclic, polycyclic, and heterocyclic;

$R_l$, and $R_m$ are each hydrocarbon radicals, which may share a covalent bond, selected from the group consisting of hydrogen, C1–C24 alkyl, aryl, arylalkyl, monocyclic, bicyclic, monoheterocyclic, and biheterocyclic wherein one of the rings bonded to Boron is non-heterocyclic;

i equals an integer between 0 and 2;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3, wherein the alkyl substituted metal hydroborate is selected from the group consisting of lithium 9-boratabicyclo[3.3.1]-nonane, lithium 9,9-dimethoxy-9-boratabicyclo[3.3.1]-nonane, dichloroaluminum disiamylborohydride, dichloroaluminum disiamyldiiso-propoxyborate, lithium methylborohydride, lithium methyltrimethoxyborate, sodium thexylmonoiso-propoxyborohydride, sodium thexyldiisopropoxyborohydride, sodium thexyltri-isopropoxyborohydride, sodium thexylborohydride, sodium diisopino-campheyldicycohexoxyborate, sodium diisopino-campheylborohydride, bromomagnesium phenyl-borohydride, bromomagnesium phenyl-monothexoxy-borohydride, bromomagnesium phenyldithexoxyborohydride, bromomagnesium phenyltri-thexoxyborate, zinc monoisopinocampheylborohydride, zinc monoisopinocampheyltriethoxyborate, magnesium dicyclohexylborohydride, and magnesium dicyclohexyldin-hexoxyborate.

7. A process for producing an alkyl substituted metal hydroborate reducing agent of the formula $X_iM[R_lR_mB(AR_jR_k)_{p+1-r}H_r]_{n-i}$ comprising: reacting an alkylborane having the formula $R_lR_mBH_p$ with greater than 10%, based on the molar content of the alkylborane, of a metal salt of the formula $X_iM(AR_jR_k)_{n-i}$, wherein:

X is a halogen;

M is a metal;

A is selected from the group consisting of oxygen, sulfur and nitrogen;

$R_j$, $R_k$, $R_l$, and $R_m$ are each hydrocarbons selected from the group consisting of hydrogen, C1–C24 alkyl, aryl, arylalkyl, monocyclic, polycyclic, and heterocyclic radicals, wherein $R_j$ and $R_k$ may share a covalent bond, and $R_l$ and $R_m$ may share a covalent bond;

i equals an integer between 0 and 2;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3, wherein the reaction of the alkylborane with the metal salt is substantially complete within one hour at ambient temperature.

8. A process for producing an alkyl substituted metal hydroborate reducing agent of the formula $X_iM[R_lR_mB(AR_jR_k)_{p+1-r}H_r]_{n-i}$ comprising: reacting an alkylborane having the formula $R_lR_mBH_p$ with greater than 10%, based on the molar content of the alkylborane, of a metal salt of the formula $X_iM(AR_jR_k)_{n-i}$, wherein:

X is a halogen;

M is a metal;

A is selected from the group consisting of oxygen, sulfur and nitrogen;

$R_j$, $R_k$, $R_l$, and $R_m$ are each hydrocarbons selected from the group consisting of hydrogen, C1–C24 alkyl, aryl, arylalkyl, monocyclic, polycyclic, and heterocyclic radicals, wherein $R_j$ and $R_k$ may share a covalent bond, and $R_l$ and $R_m$ may share a covalent bond;

i equals an integer between 0 and 2;

n equals an integer between 1 and 4, provided that i and n are limited by the valence of the metal;

j and k each equal an integer between 0 and 1, provided that the sum of j and k is at least 1;

l and m each equal an integer between 0 and 1, provided that the sum of l and m is at least 1 when A is oxygen;

p equals 3 minus the sum of l and m; and r equals an integer between 0 and 3, wherein the alkyl substituted metal hydroborate reducing agent produced disproportionates to produce a heterogeneous reducing agent system.

* * * * *

UNITED STATES PATENT AND TRADEMARK OFFICE
CERTIFICATE OF CORRECTION

PATENT NO. : 5,488,122　　　　　　　　　　　Page 1 of 4
DATED : January 30, 1996
INVENTOR(S) : T.J. Jackson It is certified that error appears in the above-indentified patent and that said Letters Patent is hereby corrected as shown below:

ON THE TITLE PAGE:

Item [56]　Refs. Cited Other Pubs.　Insert --Goralski et al., "Hydroboration. 81. Synthesis of 2-(Dialkylamino)boronic Esters and Acids via Hydroboration of Enamines. A Convenient Preparation of β-Dialkylamino Alcohols," The Journal of Organic Chemistry, Volume 52, No. 18, 1987, pp. 4014-4019.--.

| COLUMN | LINE | |
|---|---|---|
| 10 (Claim 1, | 43 line 23) | "l" should read -- $\ell$ --. |
| 10 (Claim 1, | 44 line 24) | First occurrence of "l" should read -- $\ell$ --. |
| 10 (Claim 1, | 45 line 25) | "l" should read -- $\ell$ --. |
| 10 (Claim 2, | 60 line 14) | Before $R_l$" insert --and--. |
| 11 (Claim 2, | 1 line 27) | "l" should read -- $\ell$ --. |
| 11 (Claim 2, | 2 line 28) | First occurrence of "l" should read -- $\ell$ --. |

UNITED STATES PATENT AND TRADEMARK OFFICE
CERTIFICATE OF CORRECTION

PATENT NO. : 5,488,122
DATED : January 30, 1996
INVENTOR(S) : T.J. Jackson

It is certified that error appears in the above-indentified patent and that said Letters Patent is hereby corrected as shown below:

COLUMN  LINE 11  3  "l" should read -- $\ell$ --.
(Claim 2, line 29)

11  48  "l" should read -- $\ell$ --.
(Claim 3, line 25)

11  49  First occurrence of "l" should read -- $\ell$ --.
(Claim 3, line 26)

11  50  "l" should read -- $\ell$ --.
(Claim 3, line 27)

12  8  "l" should read -- $\ell$ --.
(Claim 4, line 22)

12  9  First occurrence of "l" should read -- $\ell$ --.
(Claim 4, line 22)

12  10  "l" should read -- $\ell$ --.
(Claim 4, line 24)

12  54  "l" should read -- $\ell$ --.
(Claim 5, line 22)

UNITED STATES PATENT AND TRADEMARK OFFICE
CERTIFICATE OF CORRECTION

PATENT NO. : 5,488,122  Page 3 of 4
DATED : January 30, 1996
INVENTOR(S) : T.J. Jackson It is certified that error appears in the above-indentified patent and that said Letters Patent is hereby corrected as shown below:

| COLUMN | LINE | |
|---|---|---|
| 12 (Claim 5, | 55 line 23) | First occurrence of "l" should read -- $\ell$ --. |
| 12 (Claim 5, | 56 line 24) | "l" should read -- $\ell$ --. |
| 13 (Claim 6, | 13 line 21) | "l" should read -- $\ell$ --. |
| 13 (Claim 6, | 14 line 22) | First occurrence of "l" should read -- $\ell$ --. |
| 13 (Claim 6, | 15 line 23) | "l" should read -- $\ell$ --. |
| 14 (Claim 7, | 9 line 21) | "l" should read -- $\ell$ --. |
| 14 (Claim 7, | 10 line 22) | First occurrence of "l" should read -- $\ell$ --. |
| 14 (Claim 7, | 11 line 23) | "l" should read -- $\ell$ --. |

UNITED STATES PATENT AND TRADEMARK OFFICE
CERTIFICATE OF CORRECTION

PATENT NO. : 5,488,122            Page 4 of 4
DATED : January 30, 1996
INVENTOR(S) : T.J. Jackson It is certified that error appears in the above-indentified patent and that said Letters Patent is hereby corrected as shown below:

| COLUMN | LINE | |
|---|---|---|
| 14 (Claim 8, | 40 line 21) | "l" should read -- $\ell$ --. |
| 14 (Claim 8, | 41 line 22) | First occurrence of "l" should read -- $\ell$ --. |
| 14 (Claim 8, | 42 line 21) | "l" should read -- $\ell$ --. |

Signed and Sealed this

Fourteenth Day of May, 1996

Attest:

BRUCE LEHMAN

*Attesting Officer*          *Commissioner of Patents and Trademarks*